United States Patent [19]
Stines

[11] Patent Number: 5,290,260
[45] Date of Patent: Mar. 1, 1994

[54] ROTATIONAL PRESSURE DRIVE FOR A MEDICAL SYRINGE

[75] Inventor: Joseph R. Stines, Poland, Ind.

[73] Assignee: Vance Products Incorporated, Spencer, Ind.

[21] Appl. No.: 960,022

[22] Filed: Oct. 13, 1992

Related U.S. Application Data

[63] Continuation-in-part of Ser. No. 708,673, May 31, 1991, Pat. No. 5,160,327.

[51] Int. Cl.$^5$ ............................................. A61M 5/315
[52] U.S. Cl. ..................................... 604/224; 222/390
[58] Field of Search ................. 604/99, 97, 155, 154, 604/151, 131, 218, 224, 233; 222/319, 320, 390

[56] References Cited

U.S. PATENT DOCUMENTS

| | | | |
|---|---|---|---|
| 2,461,211 | 2/1949 | Guthrie | 229/390 |
| 4,634,431 | 1/1987 | Whitney et al. | 222/390 |
| 4,738,826 | 4/1988 | Harris | 222/390 |
| 4,743,230 | 5/1988 | Nordquest | 604/99 |
| 4,758,223 | 7/1988 | Rydell | 604/98 |
| 4,919,121 | 4/1990 | Rydell et al. | 604/97 |
| 4,940,459 | 7/1990 | Noce | 604/99 |
| 5,137,514 | 8/1992 | Ryan | 604/224 |

Primary Examiner—John G. Weiss
Attorney, Agent, or Firm—Richard J. Godlewski

[57] ABSTRACT

A rotational pressure drive for filling a medical syringe with a fluid and obtaining, maintaining, and releasing a desired fluid pressure within the syringe. The commercially available medical syringe includes a barrel with a plunger extending therein. Extending laterally and radially about the proximal end of the syringe barrel are several flanges. The rotational pressure drive comprises a hollow cylindrical chamber with a partially closed, proximal end with an opening therethrough. The drive further includes an axial extension member extending through the opening in the partially closed end for engaging and urging the proximal end of the syringe plunger toward the partially closed, proximal end. The drive, in another aspect, includes a syringe plunger having a distal and a proximal portion. The distal portion is inserted into the syringe barrel with the proximal portion extending through the opening of the partially closed, proximal portion of the drive. Positioned circumferentially and longitudinally along the chamber are pluralities of internal threads with individual starts for engaging the radially extending flanges of the syringe barrel. The plunger or axial extension member of the drive is pulled toward the partially closed, proximal end of the drive to fill the syringe with fluid. The flanges of the syringe barrel are rotationally engaged with the starts of the internal thread pluralities for advancement into the passageway of the drive. As the hollow chamber of the pressure drive is rotated with respect to the syringe barrel, the plunger is pushed into the syringe barrel to obtain and maintain a desired fluid pressure therein.

20 Claims, 6 Drawing Sheets

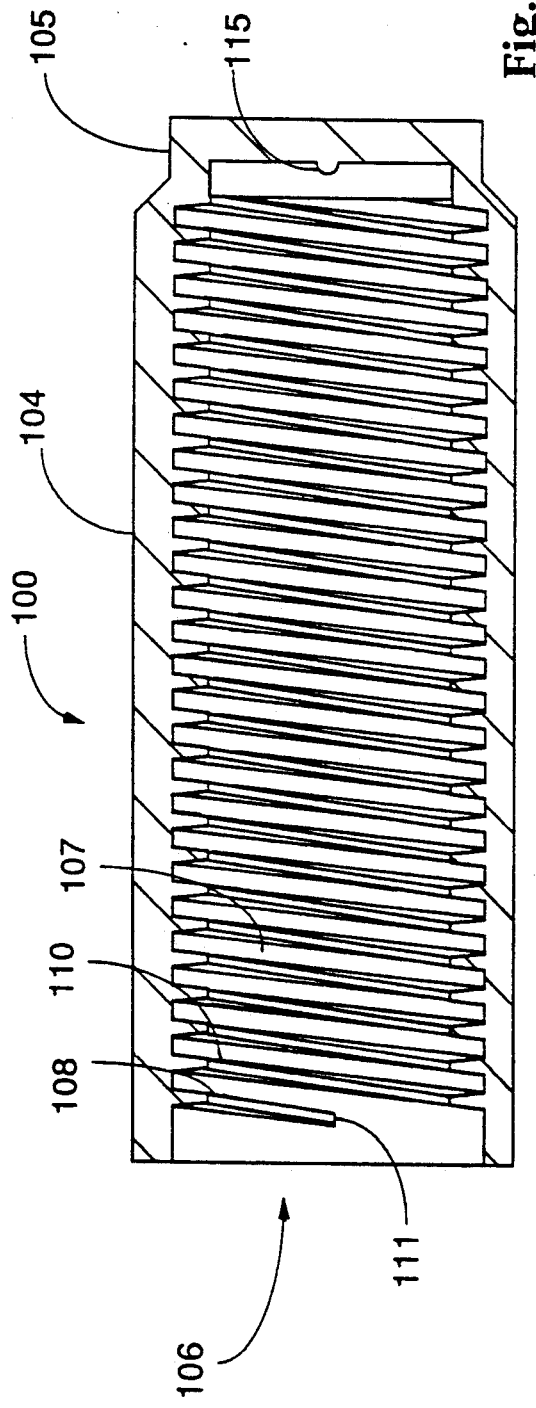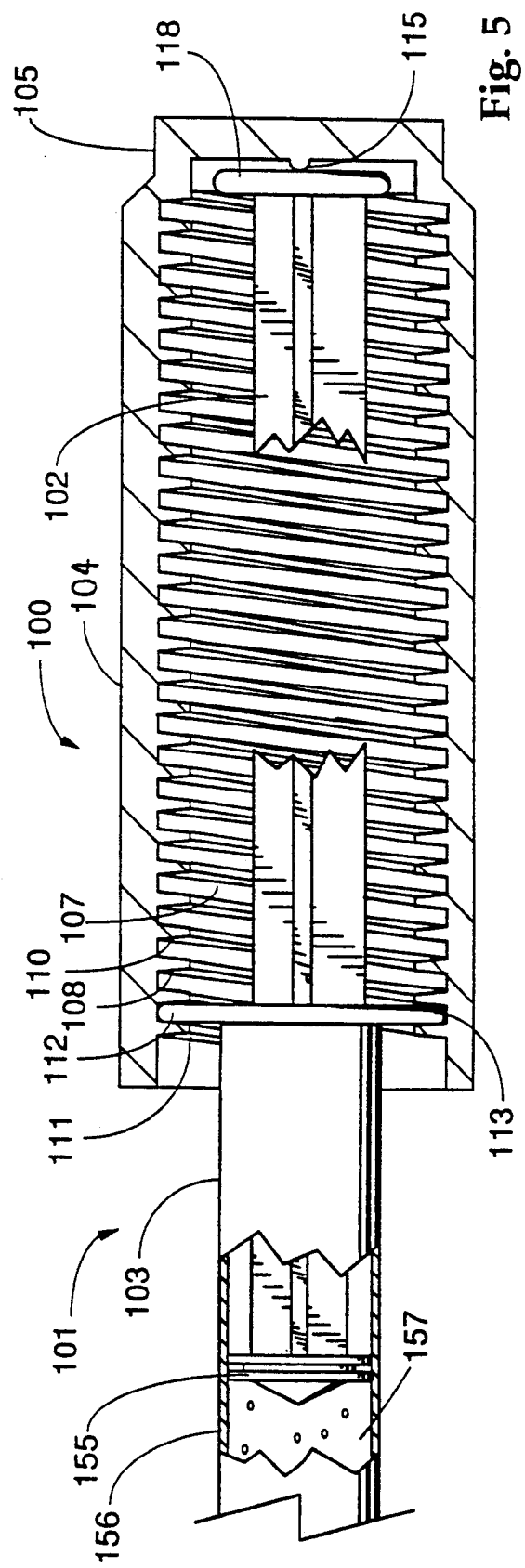

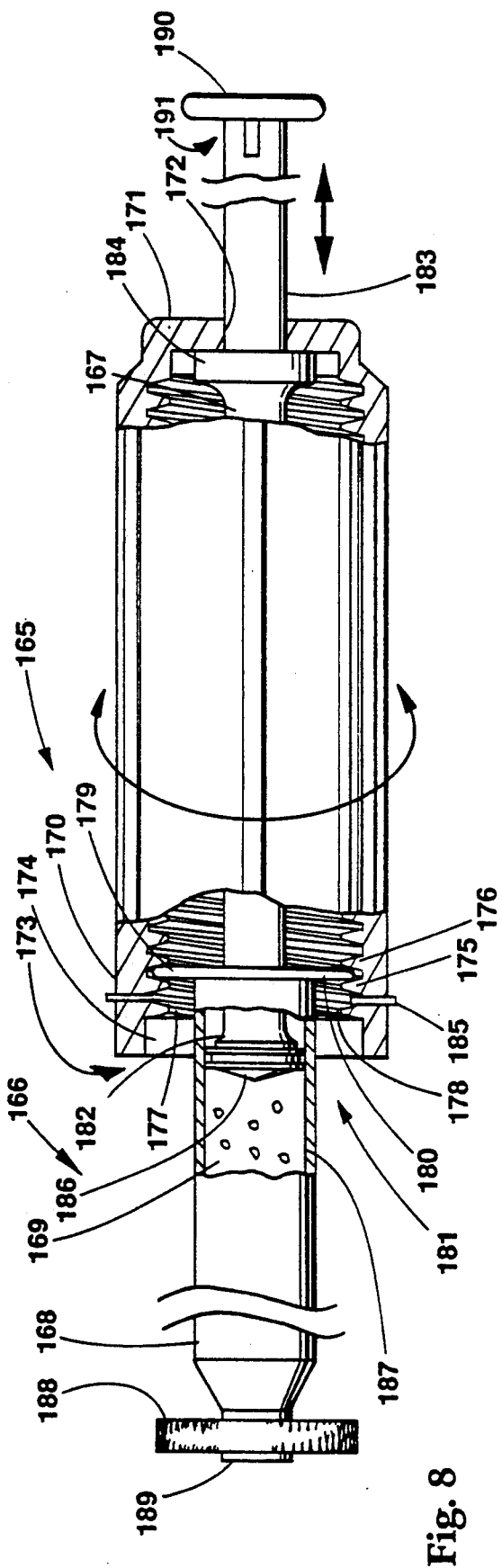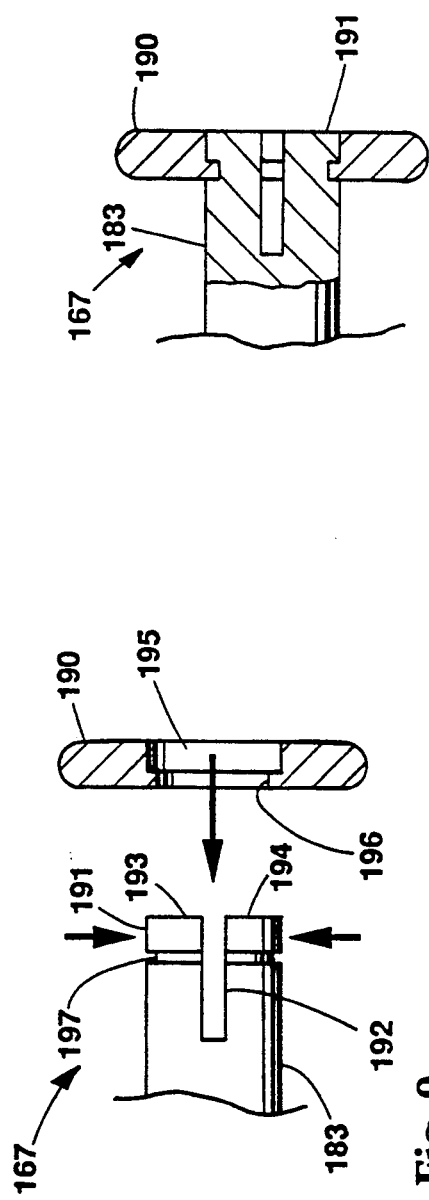
Fig. 8
Fig. 10
Fig. 9

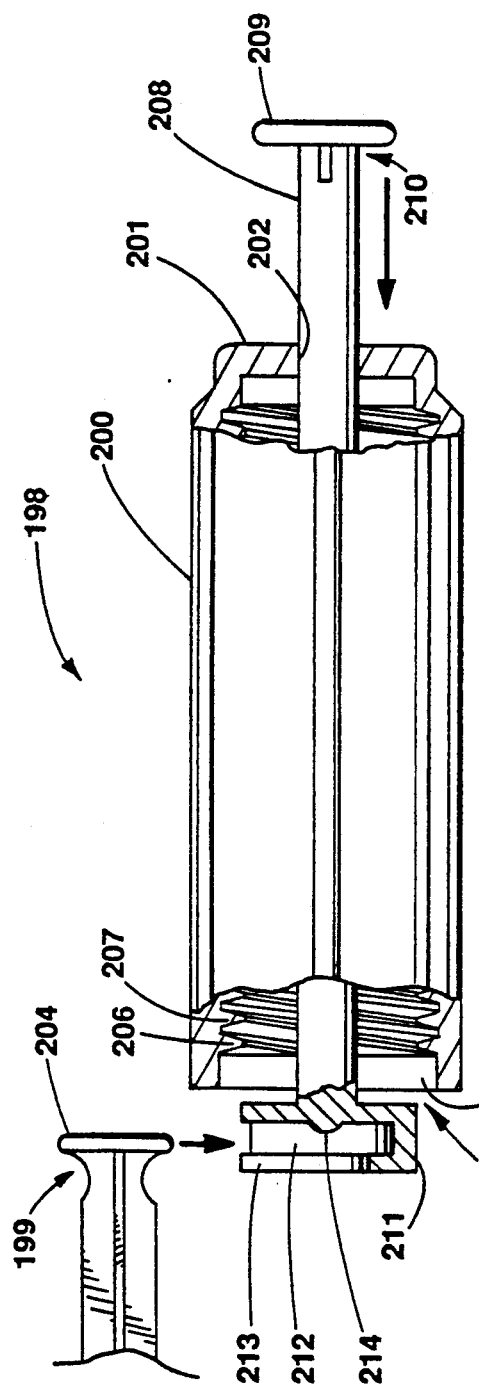
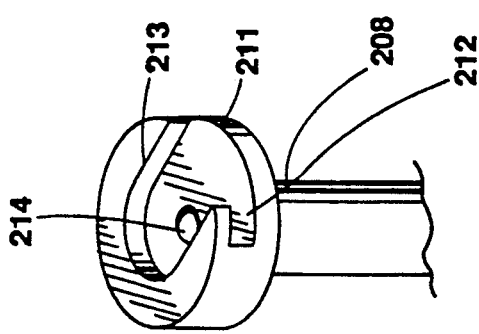
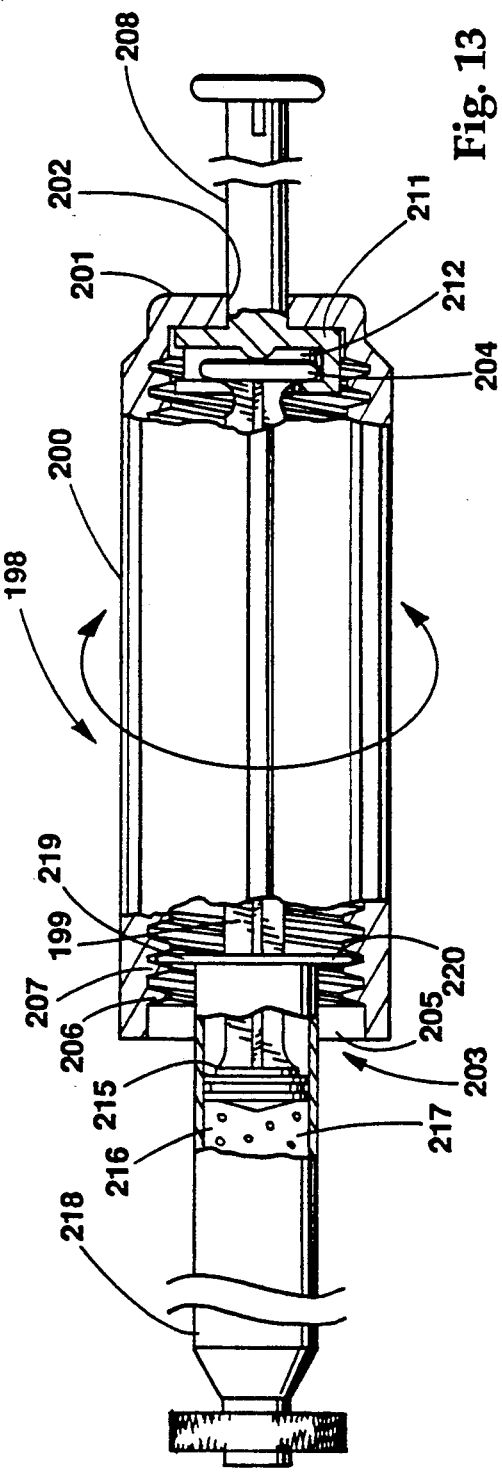
Fig. 11
Fig. 12
Fig. 13

ROTATIONAL PRESSURE DRIVE FOR A MEDICAL SYRINGE

CROSS-REFERENCE TO RELATED APPLICATIONS

This application is a continuation-in-part of pending application Ser. No. 07/708,673, filed May 31, 1991 now U.S. Pat. No. 5,160,327.

TECHNICAL FIELD

This invention relates generally to medical devices for obtaining, maintaining, and releasing fluid pressures in a syringe and, in particular, to a device for threadably engaging the external flanges of a syringe for obtaining high fluid pressures in the syringe chamber.

BACKGROUND OF THE INVENTION

High fluid pressures are required for the inflation of balloons used in medical procedures such as angioplasty and radial dilation of the urethra. The balloons are typically inflated for an extended period of time using a syringe filled with fluid. However, maintaining high fluid pressures for an extended period of time is difficult by simply applying manual force to a commercially available syringe.

One approach to this problem is to use a custom-made or modified syringe. All of these syringes commonly include an outer, internally threaded member and an inner, externally threaded member for rotational advancement of the plunger in a syringe barrel.

A disadvantage of each of these custom-made or modified syringes is that they are relatively expensive to manufacture in comparison to standard, commercially available syringes. Another disadvantage is that these syringes are more complicated to use than a standard syringe. Therefore, the physician has to become skilled at operating the device. The physician's familiarity with the device is also critical for maintaining or releasing pressure when a threshold is reached. A timely release prevents bursting the balloon or overdilating tissue. Yet another disadvantage is that these custom-made syringes are fitted with pressure gauges or indicator rods that require visual monitoring by the physician during use. The physician must actuate the modified syringe while watching a pressure indicator for a threshold pressure to be obtained. When the threshold is obtained, these custom-made syringes are manually operated for permitting fluid to exit the syringe chamber, thereby decreasing the fluid pressure therein.

Another prior art device utilizes an internally threaded outer sleeve that fixedly engages the radial projections at the proximal end of a standard syringe barrel. The device includes an externally threaded plunger that attaches to the proximal end of a standard syringe plunger for longitudinal movement of the syringe plunger with respect to the pair of radial projections at the proximal barrel end. A problem with this device is that it is expensive to manufacture. From a user's perspective, the device is large, heavy, and cumbersome, and therefore difficult and inconvenient to use.

Another disadvantage of these prior art devices is that the plunger of the syringe must be disengaged from the device to fill the syringe barrel. Alternatively, these threaded devices must be rotated to withdraw the plunger from the distal end of the barrel to fill the syringe with fluid. This is particularly annoying and time consuming when the technician or physician has initially engaged the pressure device with the syringe and forgot to initiate filling of the syringe barrel with fluid.

SUMMARY OF THE INVENTION

The foregoing problems are solved and a technical advance is achieved in an illustrative rotational pressure drive for engaging a standard, commercially available medical syringe and obtaining, maintaining, and releasing a desired fluid pressure therein. The drive comprises an elongated member such as a hollow cylindrical chamber having a passageway extending longitudinally between a closed end for engaging the proximal end of the syringe plunger and an open end for receiving the plunger and extending it through the passageway to the closed end. The drive further includes first and second pluralities of internal threads extending radially into and longitudinally along the passageway for engaging the flanges extending radially and laterally from the proximal end of the syringe barrel. Use of the pressure drive involves fully extending the plunger proximally from the syringe barrel and inserting the extended plunger into the open end of the drive, through the passageway, and to the closed end. The syringe barrel flanges engage the individual starts of the first and second pluralities of internal threads. The drive is then advantageously rotated with respect to the syringe barrel to thread the flanges into the passageway of the drive and to push the plunger into the syringe barrel. As the plunger is pushed into the syringe barrel, the fluid pressure within the barrel is increased. Any desired pressure may be maintained in the barrel depending on how far the flanges of the syringe are threaded into the passageway of the drive. A pressure limiting assembly is attached to the distal end of the syringe barrel, which releases fluid from the syringe when a threshold pressure is obtained.

A departure in the art is that the internal threads of the pluralities are a modified form of an Acme thread with multiple starts. The crest and root of an Acme thread are typically of the same width or thickness, with each thread having a flank surface angle of approximately 14.5 degrees. The threads of the present invention have a crest thickness that is different from the width of the thread root. Furthermore, the pluralities of the internal threads are positioned alternatingly between each other with each plurality having a separate start. The first and second starts of the pluralities are opposite each other about the open end of the passageway for engaging the diametrically opposed flanges of a standard, commercially available syringe. The multiple starts of the threads advantageously engage the flanges of the syringe without distorting or deforming the flanges as they are threaded into the passageway. The thread root width preferably matches the width of the syringe barrel flanges with the flank surface angle being significantly reduced from that of an Acme thread for advantageously advancing the flanges without distortion within the passageway of the drive. Preferably this flange surface angle is 2 degrees for minimizing distortion of the syringe barrel flanges, reducing rotational force, and reducing thread thickness.

Each plurality of internal threads comprises a continuous helix of which the threads of the pluralities are positioned alternatingly between each other.

The passageway includes a minor diameter slightly larger than that of the plunger cross-section for permitting insertion through the passageway of the drive and a major diameter approximating the largest radial dimension of the flanges. Thus, the major and minor diameters bound the height of the internal threads. Advantageously, the height of the various thread pluralities may be varied depending on the radial dimension of each syringe flange. Furthermore, the root between adjacent threads of the pluralities may also be varied to accommodate various thickness flanges.

Positioned about the closed end of the elongated member and extending radially into the passageway along the longitudinal axis thereof is a projection for pivotally engaging the proximal end of the plunger during rotation of the drive with respect to the syringe barrel. This advantageously prevents distortion or deformation of the plunger during rotation of the drive, thus preventing loss or leakage of fluid from the syringe barrel and variations in fluid pressure levels.

The device further includes a plurality of reinforcements extending longitudinally about the outer surface of the drive for minimizing the bulk of the drive, while maintaining the structural integrity and rigidity of the drive. Also included is a pressure relief assembly including a cylinder and a spring actuated piston positioned within the cylinder attached about the distal end of the syringe for advantageously limiting the fluid pressure within the syringe. This prevents bursting a treatment balloon as well as overdilating or traumatizing tissue.

In another aspect, the rotational pressure drive is considered a plurality of internal threads having multiple first and second starts for engagement respectively of the flanges of the syringe barrel. Each thread of the plurality has a predetermined height, a crest with a predetermined thickness, along with a root having a predetermined width to match the thickness of the syringe barrel flanges.

The foregoing problems of filling a syringe barrel with a fluid are solved and a technical advance is achieved in an illustrative rotational pressure drive for engaging a standard, commercially available medical syringe and obtaining, maintaining, and releasing a desired fluid pressure therein. The pressure drive comprises an elongated member having a partially closed end including an opening therein and an axial extension member movable through the opening of the partially closed end for pulling the plunger through the passageway of the elongated member toward the partially closed end. Pulling the plunger through the passageway toward the partially closed end advantageously facilitates filling the syringe barrel with a fluid without having to operate any other portion of the pressure device. The drive also comprises pluralities of internal threads for engaging the radially and laterally extending flanges of the syringe.

The method of controlling the pressure in the syringe with the aforementioned drive includes engaging the plunger of the syringe with the axial extension member, engaging the flanges of the syringe with the internal threads, and pulling the plunger toward the partially closed end of the elongated member with the axial extension member. The method also includes rotating the elongated member of the drive with respect to the syringe to engage the plunger with the partially closed end of the elongated member. The step of pulling the plunger with the axial extension member further includes advantageously filling the barrel with a fluid without having to rotate or disengage the internal threads of the drive with the syringe flanges.

In another aspect of the rotational pressure drive of the present invention, the drive comprises a plunger having a distal portion, a proximal portion, and a radial projection extending laterally therefrom between the distal and proximal portions. The elongated member of the drive has a partially closed end including an opening therein for extension of the proximal portion of the plunger therethrough. The partially closed end and opening form means for engaging the radial projection of the plunger and controlling the pressure of a fluid in the syringe barrel. The radial projection also permits the syringe barrel to be readily filled with a fluid without again having to disengage the plunger from the pressure drive or rotating the internal threads of the drive with respect to the syringe barrel flanges. The method of controlling the pressure in a syringe with this aspect of the invention includes the steps of inserting the distal portion of the plunger into the barrel of the syringe, engaging the flanges of the barrel with the internal threads of the elongated member, and pulling the proximal portion of the plunger through the opening of the partially closed end of the elongated. The method of controlling the pressure also includes rotating the drive with respect to the syringe to engage the radial projection of the plunger with the partially closed end of the elongated member. The step of pulling the proximal portion of the plunger through the partially closed end includes advantageously filling the barrel with a fluid without having to disengage the syringe barrel with the threads of the drive.

BRIEF DESCRIPTION OF THE DRAWING

FIG. 4 depicts a longitudinal, cross-sectional view of the pressure drive of FIG. 2 along the line 4—4;

FIG. 5 depicts the pressure drive of FIG. 4 with a medical syringe positioned therein;

FIG. 8 depicts a partially sectioned side view of another aspect of the rotational pressure drive of the present invention;

FIG. 9 depicts the disassembled proximal end of the plunger of the pressure drive of FIG. 8;

FIG. 10 depicts the assembled proximal end of the plunger of FIG. 8;

FIG. 11 depicts a partially sectioned side view of still another aspect of the rotational pressure drive of the present invention;

FIG. 12 depicts a pictorial view of the distal end of the axial extension member of the pressure drive of FIG. 11; and FIG. 13 depicts the rotational pressure drive of FIG. 11 with the axial extension member thereof engaging the proximal, partially closed end of the drive.

DETAILED DESCRIPTION

Figure 1:
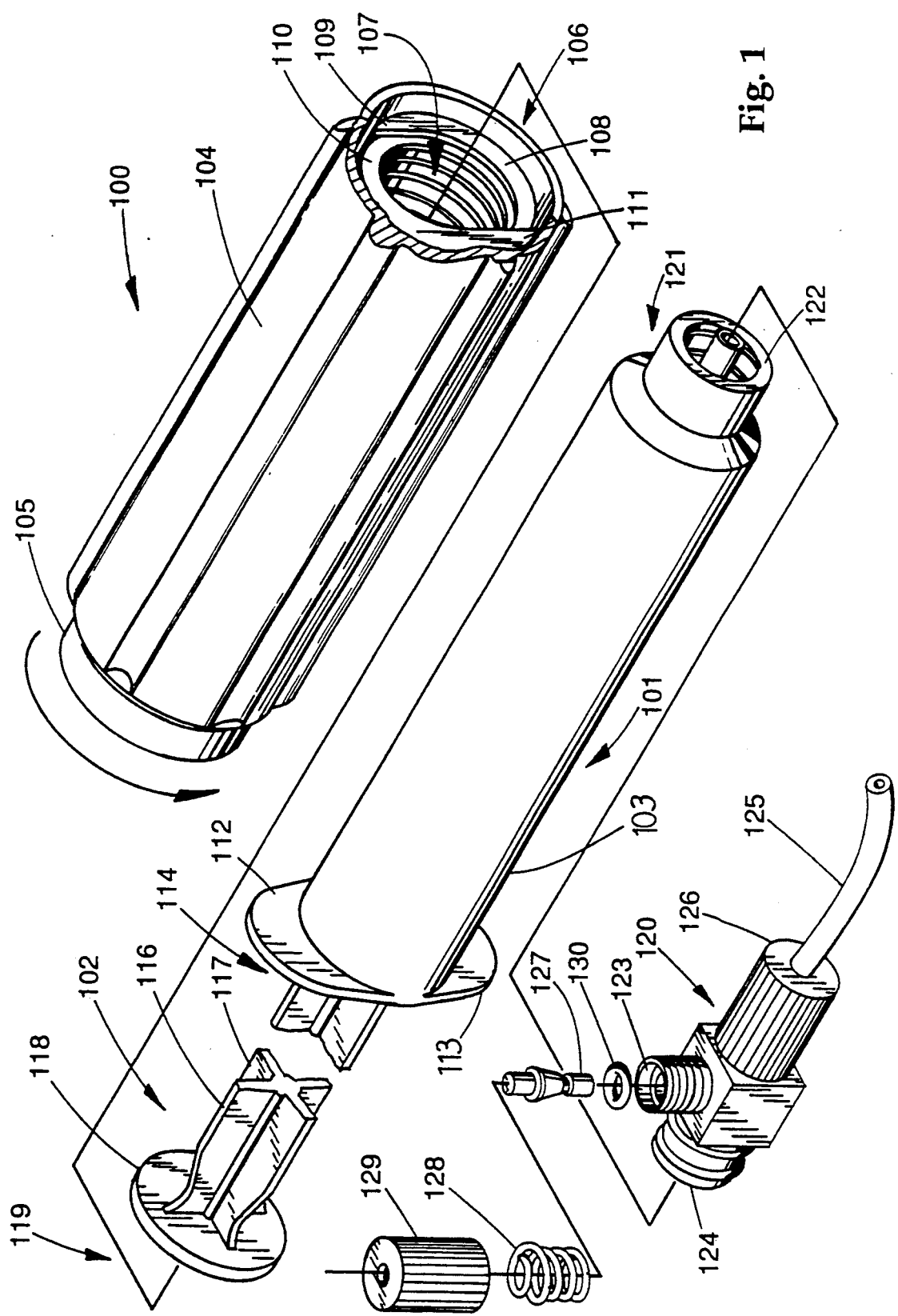
FIG. 1 depicts the rotational pressure drive and pressure relief assembly of the present invention for a medical syringe.

FIG. 1 depicts rotational pressure drive 100 that is positionable about and rotationally engageable with a standard, commercially available, 10 cc syringe 101 for engaging and pushing syringe plunger 102 into syringe barrel 103 to control the pressure of a fluid contained therein. The rotational pressure drive comprises elongated member 104 such as a hollow cylindrical chamber. The elongated member of the drive has closed proximal end 105 for engaging proximal end 119 of plunger 102, open distal end 106 for receiving the plunger, and hollow passageway 107 extending longitudinally between the open and closed ends for passage of the plunger therethrough to the closed end. The drive also includes a first plurality of internal threads 108 with start 109 and a second plurality of internal threads 110 with start 111 for engaging diametrically opposed syringe barrel flanges 112 and 113. These flanges extend radially and laterally from proximal end 114 of syringe barrel 103. Internal thread pluralities 108 and 110 extend radially into and longitudinally along the outer circumference of hollow longitudinal passageway 107 for threading the syringe barrel flanges longitudinally into the passageway toward closed proximal end 105. Syringe plunger 102 includes crisscrossed elongated members 116 and 117 with disk-like flange 118 transversely positioned and molded with the crisscrossed plunger members at the proximal end thereof.

Plunger 102 of the syringe is extended proximally from open proximal end 114 of the syringe barrel and inserted into open distal end 106 of the pressure drive. The plunger is then extended through hollow passageway 107 to engage closed proximal end 105 of the drive. Diametrically opposed syringe barrel flanges 112 and 113 are inserted into the open end of the drive to engage thread starts 109 and 111, respectively. The syringe barrel and drive are rotated with respect to each other to engage and thread syringe barrel flanges 112 and 113 into internal thread pluralities 108 and 110. Rotation of the drive with respect to the syringe barrel causes closed proximal end 105 of the drive to engage and push proximal end 119 of the plunger into the syringe barrel, thus increasing the pressure of the fluid within the syringe barrel. Continued rotation of the drive with respect to the syringe barrel further increases the pressure of the fluid contained within the barrel.

The drive also includes pressure relief assembly 120 for limiting the pressure of the fluid within the syringe barrel. Pressure relief assembly 120 is connected to distal end 121 of the syringe barrel which has a female Luer lock connector 122 positioned thereat. Pressure relief assembly 120 is well-known and includes cylinder 123 that communicates with a passageway extending longitudinally through the assembly between proximally positioned, male Luer lock connector 124 and inflation tube 125 extending distally from the assembly through end cap 126. Pressure relief assembly 120 further includes a well-known cylindrical piston 127 that is positioned within cylinder 123 and forced therein with actuation spring 128 and end cap 129. An o-ring seal 130 is also positioned around the piston and within the cylinder to maintain a seal between the cylinder and piston. Actuation spring 128 exerts a force against the proximal end of the piston to maintain the piston within the cylinder. As the fluid pressure within the syringe barrel and pressure relief assembly builds up to exceed the counteracting force of the actuation spring, the piston is pushed out of the cylinder. Thus, the spring actuated piston limits the pressure within the cylinder as well as inflation tube 125 and syringe barrel 103.

Syringe 101 is a standard, well-known, and commercially available 10 cc syringe from Becton Dickinson & Company, Rutherford, New Jersey. This syringe has an outer barrel diameter of approximately, 0.630" with an overall length of 3.75". Flanges 112 and 113 extend an equal distance laterally and radially from the proximal end of the barrel and have a maximum cross-sectional dimension of 1.107" and a minimum cross-sectional dimension of 0.74". The overall length of plunger 102 is approximately 4" with the crisscrossed elongated members being approximately 0.500" in width. The disk-like flange 118 has a diameter of approximately 0.730".

Figure 2:
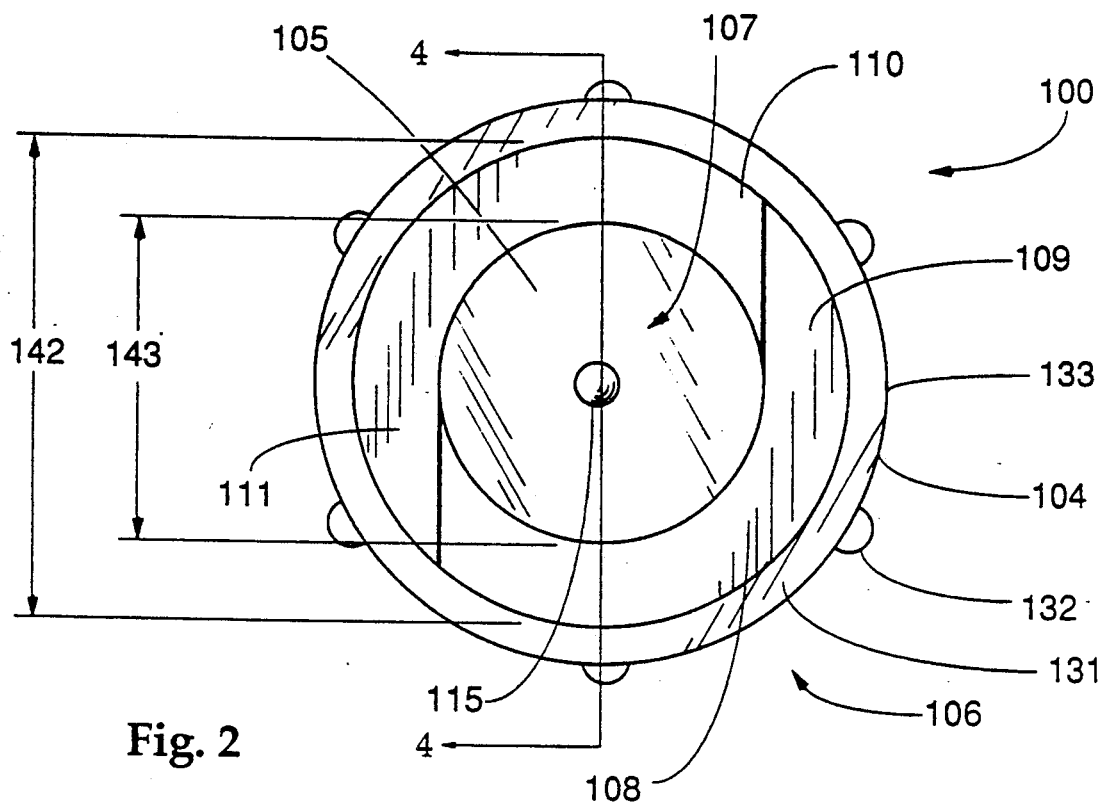
FIG. 2 depicts an end view of the pressure drive of FIG. 1.

FIG. 2 depicts an end view of drive 100 looking into open distal end 106 of elongated member 104 through longitudinal passageway 107 toward closed proximal end 105. Also depicted are first plurality of internal threads 108 with first start 109 and second plurality of internal threads 110 with second start 111. As previously indicated, starts 109 and 111 are diametrically opposite each other in the passageway about distal open end 106 of the drive. Extending from closed proximal end 105 into hollow longitudinal passageway 107 is pivot projection 115 for engaging and pushing against the proximal end of the plunger and, in particular, the disk-like plunger flange. As the drive is rotated with respect to the barrel, the plunger flange pivots about projection 115 without deforming or twisting the plunger. Also shown is elongated member wall 131 with a plurality of longitudinally positioned reinforcement ribs 132 positioned about external surface 133 of the member. The thickness of wall 131 is approximately 0.050". Longitudinal passageway 107 has a major diameter 142 of approximately 1.134" and a minor diameter 143 of approximately 0.774".

Rotational pressure drive 100 is molded from a commercially available medical grade nylon material. The overall length of the drive is approximately 3.375" with an outside surface diameter of 1.238". The six reinforcement ribs 132 are each comprised of a 0.187" diameter semicircular longitudinal rib which are spaced equally around and longitudinally along the outer surface 133 of the elongated member, which extends longitudinally for approximately 3.0". The outside diameter of closed proximal end 105 is approximately 1.017", which is annularly recessed from the outer surface of the drive and extends longitudinally for approximately 0.285".

Figure 3:
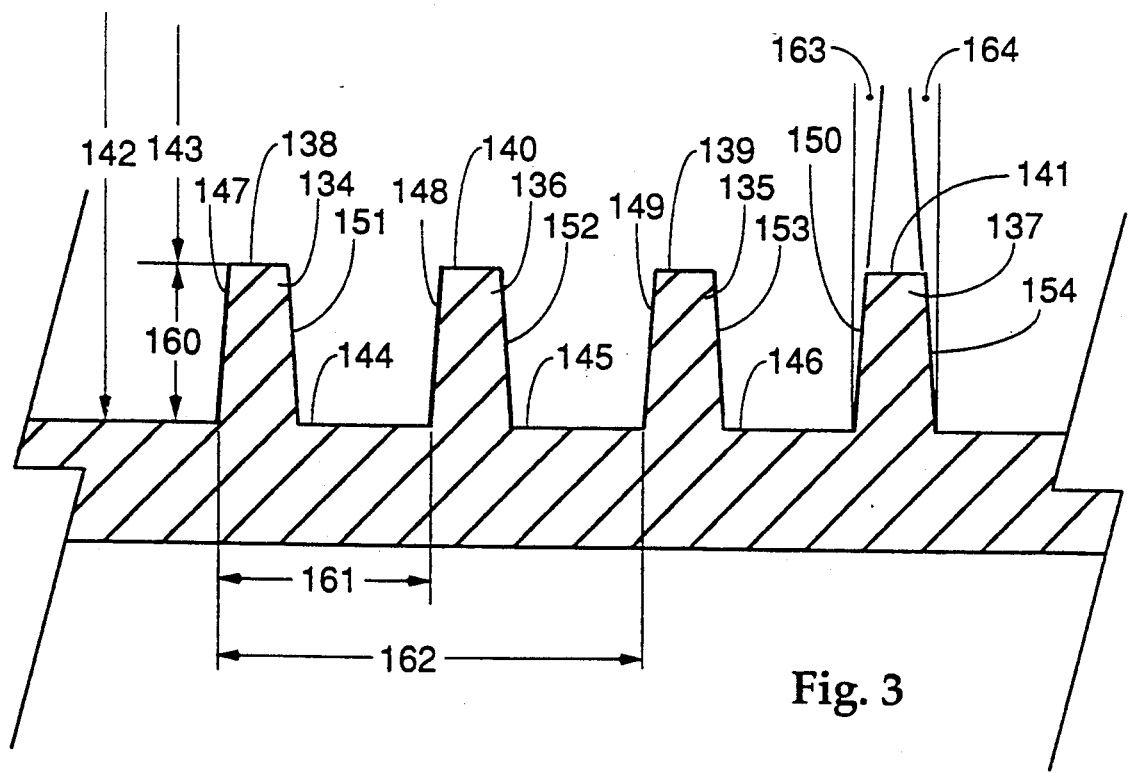
FIG. 3 depicts a cross-sectional thread profile of the pressure drive of FIGS. 1 and 2.

FIG. 3 depicts a partial, longitudinal, cross-sectional profile view of internal threads 134 and 135 of first plurality 108 and internal threads 136 and 137 of second plurality 110. Internal threads 134 and 135 of plurality 108 include respective crests 138 and 139 with a thickness of approximately 0.034" to 0.035". Crests 140 and 141 of respective internal threads 136 and 137 of second plurality 110 are also approximately 0.034" to 0.035" in thickness. Height 160 of internal threads 134–137 is equal to half the difference between major and minor diameters 142 and 143, which is approximately 0.180". Pitch 161 between internal threads 134 and 136 is approximately 0.125", whereas pitch 162 between internal threads 134 and 135 of first plurality 108 is approximately 0.250". Roots 144–146 are approximately 0.081" in width. However, the width of roots 144 and 145 may independently vary depending on the thickness of syringe barrel flanges 112 and 113. The width of internal threads 134–137 at diameter 142 of the passageway is approximately 0.044". Leading flank surfaces 147-150 of respective threads 134-137 each have a well-known flank angle 163 of approximately 2 degrees as opposed to an Acme flank angle of approximately 14.5 degrees. This angle can preferably range from 1.8 to 2.2 degrees for a 10 cc Becton and Dickinson syringe. Pressure flank surfaces 151-154 of respective internal threads 134-137 each have a predetermined flank angle 164 of approximately 2 degrees, again in contrast to a 14.5 degree Acme flank surface angle. Again, depending on the type of flanges utilized, the leading and pressure flank surfaces may have different flank angles as well as having different leading and pressure flank angles on each of the two internal thread pluralities. Alternatively, internal thread pluralities 108 and 110 may also be considered as a single plurality of threads with multiple starts 109 and 111. The aforedescribed thread profile clearly constitutes a departure and modification from that of an Acme thread profile with dual starts and equal width crests and roots. The reader is referred to *Machinery's Handbook,* Twenty-first and Twenty-third Editions, Industrial Press Incorporated, New York, New York, for a more detailed description of the terms utilized herein to describe the internal threads and their constituent parts. Many of the definitions contained therein to describe thread parts are hereby incorporated by reference.

FIG. 4 depicts a longitudinal cross-sectional view of drive 100 of FIG. 2 along the line 4—4. As shown, elongated member 104 of the drive, such as a hollow cylindrical chamber, has closed proximal end 105 and open distal end 106 with passageway 107 extending therebetween. Closed proximal end 105 has a wall thickness of approximately 0.115". Pivot projection 115, with a height of 0.025", extends into the passageway along the longitudinal axis thereof. As shown, first plurality of internal threads 108 extends almost the entire length of the passageway, and similarly, second plurality of internal threads 110 is alternatingly positioned between the threads of first plurality 108. Start 111 of second plurality of internal threads 110 begins about open distal end 106 of the passageway.

FIG. 5 depicts the longitudinal cross-sectional view of drive 100 of FIG. 4 with syringe 101 positioned within passageway 107 of elongated member 104. Plunger 102 extends proximally from syringe barrel 103 with disk-like flange 118 engaging and making contact with pivot projection 115. Syringe barrel flanges 112 and 113 are positioned in diametrically opposed roots of internal thread pluralities 108 and 110. As a result, distal end 155 of plunger 102 is pushed into chamber 156 of the syringe barrel as drive 100 is rotated with respect to syringe barrel 103. Furthermore, the pressure of fluid 157 contained within the chamber of the barrel is increased.

Figure 6:
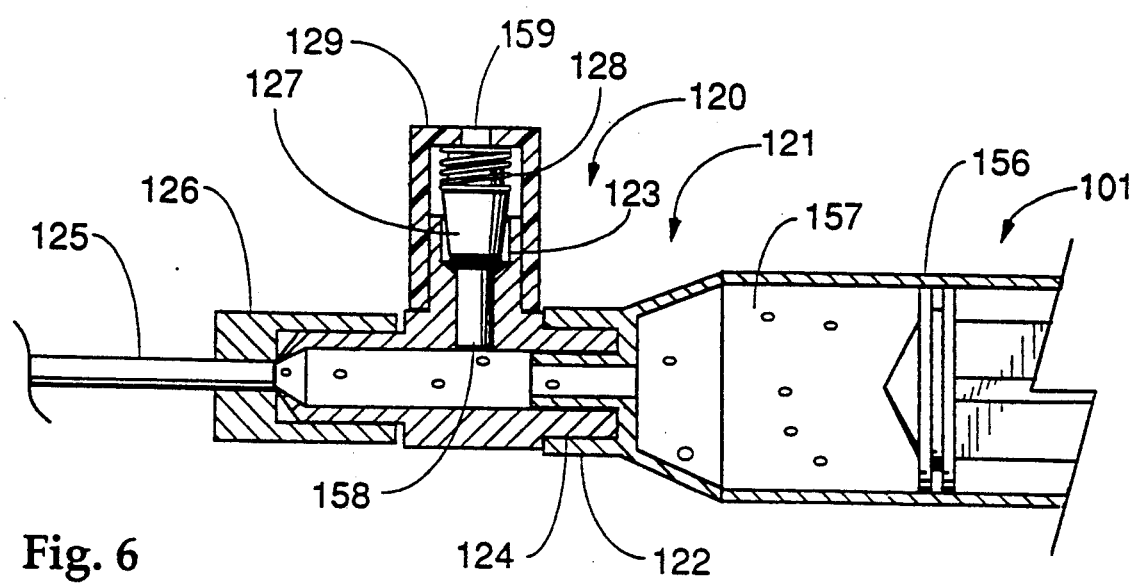
FIG. 6 depicts a partial, cross-sectional view of the pressure relief assembly of FIG. 1 attached to the distal end of a medical syringe.

FIG. 6 depicts pressure relief assembly 120 attached to distal end 121 of syringe 101 via syringe connector 122 and assembly connector 124. Extending through end cap 126 is inflation tube 125, which communicates with the interior of an angioplasty balloon or other medical dilation device (not shown). As the pressure of fluid 157 in chamber 156 of the syringe increases, a force is exerted against distal end 158 of pressure relief piston 127. When the fluid pressure exceeds the counteracting force exerted by actuation spring 128, the piston is pushed toward end cap 129 releasing fluid 157 around piston 127 and through cylinder 123 and aperture 159 of end cap 129 until the fluid pressure and spring force are once again equal.

Figure 7:
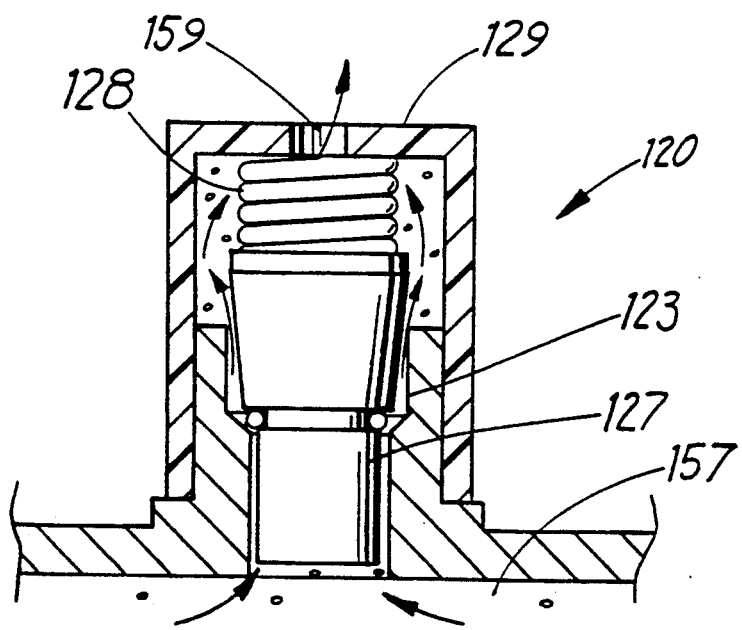
FIG. 7 depicts an enlarged partial cross-sectional view of the piston and cylinder of the pressure relief assembly of FIG. 6.

FIG. 7 is an enlarged view of cylinder 123 and piston 127 of pressure relief assembly 120. As illustrated, the pressure of fluid 157 has exceeded the force exerted by actuation spring 128, thereby pushing piston 127 out of cylinder 123, thereby releasing fluid 157 around piston 127 and through cylinder 123 and out aperture 159 of end cap 129.

FIG. 8 depicts a partially sectioned side view of rotational pressure drive 165, which represents another aspect of the present invention. Pressure drive 165 is positionable about and rotationally engageable with commercially available, 10 cc syringe 166 for pushing drive plunger 167 into syringe barrel 168 to control the pressure of fluid 169 contained within the barrel. The drive comprises elongated member 170, such as a hollow cylindrical chamber that was described previously, having a partially closed, proximal end 171 with opening 172 therethrough. The elongated member also includes open distal end 173 and hollow passage 174 extending between the proximal and distal ends for receiving and extending drive plunger 167 therethrough. The drive also includes a first plurality of internal threads 175 with start 177 and a second plurality of internal threads 176 with start 178 for engaging diametrically opposed syringe barrel flanges 179 and 180. These flanges extend radially and laterally from proximal end 181 of syringe barrel 168. The first and second plurality of internal threads with their respective starts form means for engaging respectively the laterally extending flanges of the syringe barrel. The rotational pressure drive also includes plunger 167 having a distal portion 182 and a proximal portion 183. The plunger also includes a radial projection 184 extending laterally therefrom between the distal and proximal portions for engaging partially closed, proximal end 171 for forcing distal end 186 of the plunger into chamber 187 of the syringe barrel. As the distal end of the plunger is urged into the syringe barrel chamber with the rotation of the drive about flanges 179 and 180 of the syringe barrel, fluid 169 in syringe barrel chamber 187 is compressed, thereby increasing the pressure of the fluid in the chamber. Partially closed end 171 of the elongated member and opening 172 therein form means for engaging radial projection 184 of the plunger.

Each thread of the plurality of internal threads 175 and 176 has a predetermined height, a crest having a predetermined thickness, and a root having a predetermined width as previously discussed with respect to the embodiment of FIG. 3. Each thread of the plurality of internal threads further includes a flank surface having a predetermined flank angle as also discussed with the embodiment depicted in FIG. 3. Furthermore, the alternatingly positioned internal threads of pluralities 175 and 176 include respective starts 177 and 178 positioned opposite each other about open end 173 of the elongated member of the drive. The pluralities of internal threads comprise a first and a second continuous helix of which the internal threads are positioned alternatingly between each other. Passageway 174 of elongated member 170 includes a major diameter and a minor diameter similar to the major and minor diameters 142 and 143 as depicted in and described with respect to FIG. 2. Again, the properties of the internal threads are similar to and variable as described with respect to internal threads 108 and 110 depicted in FIGS. 1-5. The drive further includes well-known expansion retaining pins 185 positioned as shown in FIG. 8 for maintaining syringe flanges 179 and 180 in passageway 174 of elongated member 170.

Rotational pressure drive 165 also includes a rotational control collar 188 threadably engaging distal end 189 of syringe barrel 168. The rotational control collar maintains purchase of the syringe barrel as the pressure drive is rotated in a clockwise manner for urging plunger 167 into syringe barrel chamber 187.

Plunger 168 of the pressure drive includes proximal end cap 190 positioned at proximal end 191 of the plunger. During assembly of the pressure drive, proximal plunger portion 183, without end cap 190, is positioned through opening 172 in partially closed, proximal end 171 of the elongated member. Once positioned through opening 172, proximal end cap 190 is snap fitted in a well-known manner onto longitudinally slotted proximal end 191 of the plunger.

FIG. 9 depicts a side view of disassembled proximal end 191 of plunger 167 of FIG. 8 with partially sectioned end cap 190. Proximal portion 183 of plunger 167 includes longitudinal slot 192 extending centrally into the plunger from proximal end 191. This provides for the radial compression of plunger members 193 and 194 inwardly to pass through ridged opening 195 of end cap 190. Extending into opening 195 is annular ridge 196 which engages annular recess 197 circumferentially positioned around proximal portion 183 near proximal end 191 and longitudinal slot 192. Proximal end cap 190 is snap fitted over the proximal end of the plunger in a well-known manner as depicted in FIG. 10.

FIG. 10 depicts a partially sectioned side view of assembled proximal end 191 of proximal plunger portion 183 of FIG. 8 with proximal end cap 190 positioned thereon.

The method of manually filling and controlling the pressure of a fluid such as 186 in a syringe barrel with drive 165 includes the following. Distal portion 182 of plunger 167 is inserted into syringe barrel 168. Elongated member 170 is urged toward the syringe barrel so that internal thread pluralities 175 an 176 with respective starts 177 and 178 of elongated member 170 engage laterally and radially extending flanges 179 and 180 of the syringe barrel. Proximal portion 183 of the plunger is pulled through opening 172 of partially closed end 171 of the elongated member to draw fluid 169 into chamber 187 of the barrel. Elongated member 170 of the drive is rotated with respect to syringe 167 to engage radial projection 184 of the plunger with the partially closed end of the elongated member. As elongated member 170 of the pressure drive is rotated with respect to the syringe barrel, distal end 186 of the plunger is urged into syringe barrel chamber 187 to compress fluid 169 and increase the pressure thereof. The rotation of the drive with respect to the syringe includes threading the flanges into the internal thread pluralities that extend into the passageway of the elongated member. Pulling the plunger through the opening of the partially closed end of the elongated member also fills the barrel chamber with fluid 169 as previously suggested.

FIG. 11 depicts rotational pressure drive 198, which represents still another aspect of the present invention for engaging and pushing syringe plunger 199 into a syringe barrel to control the pressure of a fluid contained therein. Rotational pressure drive 198 comprises elongated member 200 having a partially closed, proximal end 201 with opening 202 formed therethrough. Elongated member 200, such as a hollow chamber, includes open distal end 203 for reception of proximal end 204 of the plunger. The elongated member includes passageway 205 extending longitudinally between the open and partially closed ends for passage of the plunger therethrough. Internal thread pluralities 206 and 207 as previously described, extend radially into and longitudinally along the passageway, which forms means for engaging the radially extending flanges of a syringe barrel. Rotational pressure drive 198 also includes an axial extension member 208, which is movable through opening 202 of the partially closed, proximal end for engaging proximal end 204 of the plunger and pulling the plunger toward the partially closed, proximal end of the elongated member. The properties of the internal thread pluralities are as previously described. The axial extension member includes a proximal end cap 209 positioned at proximal end 210 of the extension member. Proximal end 210 of the extension member 208 is inserted through opening 202 of partially closed, proximal end 201 of the elongated member, and end cap 209 is snap fitted thereon in a well-known manner and as previously described with respect to FIGS. 8-10. Enlarged distal end 211 of the extension member includes a distal end chamber 212 with a U-shaped, distal opening 213 communicating with the chamber to form a well-known T-slot extending therein from the distal end thereof. Proximal end cap 204 of the plunger is inserted into the T-slot for pulling the plunger through the passageway through the partially closed, proximal end of the elongated member. Chamber 212 also includes projection 214 extending into the chamber, as depicted in FIG. 11, for engaging distal end cap 204 of plunger 199.

FIG. 12 depicts a pictorial view of enlarged distal end 211 of axial extension member 208 of the rotational pressure drive. T-slot chamber 212 is shown with U-shaped, distal end opening 213 leading thereto. Projection 214 is shown extending into the chamber, again, for engaging proximal end cap 204 of the plunger, so as to allow the plunger end cap to rotate without distortion as elongated member 200 is threaded onto the flanges of the syringe barrel.

FIG. 13 depicts a partially sectioned side view of rotational pressure drive 198 of FIG. 11 with axial extension member 208 extending through opening 202 of partially closed, proximal end 201 of the chamber. Enlarged distal end 211 of the axial extension member has distal end cap 204 of syringe plunger 199 cradled in T-slot chamber 212. The enlarged distal end of the axial extension member along with the distal end cap of the syringe plunger is depicted engaging the partially closed, proximal end 201 of elongated member 200. In this position, distal end 215 of the syringe plunger is shown fully withdrawn, having pulled fluid 216 into chamber 217 of syringe barrel 218. Internal thread pluralities 206 and 207 engage laterally and radially extending flanges 219 and 220 of the syringe barrel.

The method of manually filling and controlling the pressure in syringe barrel 218 with rotational pressure drive 198 includes the steps of engaging plunger 199 with axial extension member 208. In particular, enlarged distal end 211 of the extension member is extended from open end 203 of elongated member 200, and distal end cap 204 of syringe plunger 199 is inserted into T-slot chamber 212. The method further includes respectively engaging internal thread pluralities 206 and 207 with flanges 219 and 220 of the syringe barrel by the longitudinal and rotational movement of elongated member 200 of the drive. Axial extension member 208 is grasped and pulled by an attendant to pull plunger 199 into passageway 205 and toward partially closed, proximal end 201 to fill syringe barrel chamber 217 with fluid 216. Elongated member 200 of the drive is then rotated with respect to the syringe to engage the plunger with the partially closed end of the elongated member. Once engaged, the elongated member of the drive is further rotated with resect to the syringe barrel to urge distal end 215 of the syringe plunger into the syringe barrel chamber. As a result, fluid 216 in syringe barrel chamber 217 is compressed and the pressure thereof increased.

It is to be understood that the above-described rotational pressure drive is merely an illustrative embodiment of the principles of this invention and that other rotational pressure drives may be devised by those skilled in the art without departing from the spirit and scope of this invention. In particular, the height of the threads as well as the root and crest may be varied according to the length, width, and thickness of the radially extending syringe flanges. These may be varied to accommodate two or more flanges with a corresponding number of starts and pluralities of internal threads within the passageway of the hollow elongated member. It is also contemplated that the threads about the open end of the chamber may be spaced closer together to provide less force to initiate the initial progress of the syringe plunger in the syringe barrel. As the pressure in the syringe barrel is increased, the threads positioned further in the passageway of the drive may be spread apart to provide greater longitudinal movement through the hollow passageway. In the preferred embodiment, one rotation of the drive corresponds to a decrease in the volume of the fluid within the syringe barrel of 1 cc. The pitch of the threads may be lengthened or shortened to vary the amount of fluid compression within the syringe barrel. It is also contemplated that the actuation spring of the pressure relief assembly may also be varied to provide different threshold release pressures along with other pressure relief mechanisms being attached to the distal end of the syringe barrel. In the preferred embodiment, the rotational pressure drive has been designed for a commercially available and commonly used 10 cc syringe. The dimensions of the drive may be varied to accommodate any commercially available syringe without any modification to the syringe, therefore making the use of this drive very economical and efficient without having to modify the structure of the syringe in any aspect. It is also contemplated that other forms of multiple start threads, such as the buttress, square, and other threads or combinations thereof may also be modified for the rotational pressure drive. The plunger of the syringe can be engaged with any type of axial extension member to draw the plunger and f ill the syringe barrel with fluid. The drive can also be fabricated to include any type of plunger insertable into a commercially available syringe barrel that can also be pulled or drawn through the partially closed end of the drive to f ill the syringe barrel with fluid.

What is claimed is:

1. A rotational pressure drive f or a syringe having a barrel, a plunger positioned through a proximal end of said barrel, and first and second flanges extending radially and laterally from said proximal end of said barrel, comprising:

an elongated member having a partially closed end including an opening therein, an open end for reception of said plunger, and a passageway extending longitudinally between said open and partially closed ends for passage of said plunger therethrough;

axial extension means moveable through said opening of said partially closed end for pulling said plunger through said passageway toward said partially closed end; and first and second pluralities of internal threads extending radially into and longitudinally along said passageway forming means for engaging said first and second flanges, respectively.

2. The drive of claim 1 wherein the internal threads of said first and second pluralities are positioned alternatingly between each other.

3. The drive of claim 2 wherein said first and second pluralities of internal threads include respective first and second starts positioned opposite each other about said open end.

4. The drive of claim 1 wherein said first and second pluralities of internal threads comprise respectively a first and a second continuous helix of which the internal threads are positioned alternatingly between each other.

5. The drive of claim 1 wherein said passageway includes a major diameter and a minor diameter bounding said first and second pluralities of internal threads.

6. The drive of claim 5 wherein each thread of said first plurality includes a first flank surface having a first predetermined flank angle and wherein each thread of said second plurality includes a second flank surface having a second predetermined flank angle.

7. The drive of claim 6 wherein each thread of said first plurality includes a first crest having a first predetermined thickness and wherein each thread of said second plurality includes a second crest having a second predetermined thickness.

8. The drive of claim 7 wherein adjacent threads of said first and second pluralities include a root therebetween having a predetermined width.

9. The drive of claim 8 wherein each thread of said first plurality has a first predetermined height.

10. The drive of claim 9 wherein each thread of said second plurality has a second predetermined height.

11. The drive of claim 1 further comprising a plurality of reinforcements extending longitudinally about an outer surface of said drive.

12. A method of controlling the pressure in a syringe with said drive of claim 1, said syringe having a barrel, a plunger positioned through a proximal end of said barrel, and first and second flanges extending radially and laterally from said proximal end of said barrel, said method comprising the steps of:

engaging said plunger with said axial extension means;

engaging said first and second flanges with said first and second pluralities of internal threads, respectively;

pulling said plunger toward said partially closed and with said axial extension means; and rotating said elongated member with respect to said syringe to engage said plunger with said partially closed end of said elongated member.

13. The method of claim 12 wherein said pulling includes filling said barrel with a fluid.

14. A rotational pressure drive for a syringe having a barrel and first and second flanges extending radially and laterally from a proximal end of said barrel, comprising:

a plunger having a distal portion, a proximal portion, and a radial projection extending laterally therefrom between said distal and proximal portions;

an elongated member having a partially closed end including an opening therein for extension of said distal portion of said plunger therethrough and forming means for engaging said radial projection of said plunger, an open end for reception of said plunger, and a passageway extending longitudinally between said open and partially closed ends for passage of said plunger therethrough; and a plurality of internal threads having first and second starts forming means for engaging respectively said first and second flanges.

15. The drive of claim 14 wherein each thread of said plurality has a predetermined height, a crest having a predetermined thickness, and a root having a predetermined width.

16. The drive of claim 14 wherein each thread of said plurality further includes a flank surface having a predetermined flank angle.

17. A method of controlling the pressure in a syringe with said drive of claim 14, said syringe having a barrel and first and second flanges extending radially and laterally from a proximal end of said barrel, said method comprising the steps of:

inserting said distal portion of said plunger into said barrel of said syringe;

engaging said first and second flanges with said first and second pluralities of internal threads, respectively;

pulling said proximal portion of said plunger through said opening of said partially closed end of said elongated member; and rotating said elongated member with respect to said syringe to engage said radial projection of said plunger with said partially closed end of said elongated member.

18. The method of claim 17 wherein the step of pulling includes filling said barrel with a fluid.

19. The method of claim 17 wherein the step of rotating said elongated member includes threading said flanges into said passageway of said drive.

20. A rotational pressure drive and syringe, comprising:

a barrel having a proximal end and first and second flanges extending radially and laterally from said proximal end of said barrel, a plunger having a distal portion positioned in said barrel, a proximal portion, and a radial projection extending laterally therefrom between said distal and proximal portions, said proximal portion having an end cap at a proximal end thereof;

an elongated member having a partially closed end including an opening for extension of said proximal portion therethrough and forming means f or engaging said radial projection of said plunger between said distal and proximal portions, an open end for reception of said plunger, and a passageway extending longitudinally between said open and partially closed ends for passage of said plunger therethrough; and first and second pluralities of alternatingly positioned internal threads extending radially into and longitudinally along said passageway engaging said first and second flanges, respectively, and including respective first and second starts positioned opposite each other about said open end, each thread of said first plurality including a first flank surface having a first predetermined flank angle, a first crest having a first predetermined thickness, and a first predetermined height, each thread of said second plurality including a second flank surface having a second predetermined flank angle, a second crest having a second predetermined thickness, and a second predetermined height, adjacent threads of said first and second pluralities including a root therebetween having a predetermined width;

a plurality of reinforcements extending longitudinally about an outer surface of said drive; and first and second expansion pins extending through said elongated member near said open end and into said passageway.

* * * * *